US 11,478,565 B2

(12) United States Patent
Hernandez

(10) Patent No.: US 11,478,565 B2
(45) Date of Patent: Oct. 25, 2022

(54) DEVICE FOR EMANATING MATERIALS

(71) Applicant: Henkel AG & Co. KGaA, Duesseldorf (DE)

(72) Inventor: Robert Ruiz Hernandez, Duesseldorf (DE)

(73) Assignee: Henkel AG & Co. KGaA, Duesseldorf (DE)

(*) Notice: Subject to any disclaimer, the term of this patent is extended or adjusted under 35 U.S.C. 154(b) by 856 days.

(21) Appl. No.: 16/269,773

(22) Filed: Feb. 7, 2019

(65) Prior Publication Data

US 2019/0184050 A1    Jun. 20, 2019

Related U.S. Application Data

(63) Continuation of application No. PCT/EP2017/069441, filed on Aug. 1, 2017.

(30) Foreign Application Priority Data

Aug. 9, 2016 (EP) ..................... 16183453

(51) Int. Cl.
*H05B 3/00* (2006.01)
*H05B 3/42* (2006.01)
(Continued)

(52) U.S. Cl.
CPC ............... *A61L 9/03* (2013.01); *A01N 25/18* (2013.01); *H05B 1/0297* (2013.01); *H05B 3/0014* (2013.01); *H05B 3/06* (2013.01); *H05B 3/40* (2013.01); *H05B 3/42* (2013.01); *H05B 2203/012* (2013.01); *H05B 2203/02* (2013.01); *H05B 2203/021* (2013.01); *H05B 2203/022* (2013.01)

(58) Field of Classification Search
None
See application file for complete search history.

(56) References Cited

U.S. PATENT DOCUMENTS 4,663,315 A    5/1987    Hasegawa et al.
6,104,867 A    8/2000    Stathakis et al.
(Continued)

FOREIGN PATENT DOCUMENTS

EP        0290159 A2    11/1988
EP        0362397 A1    4/1990
(Continued)

OTHER PUBLICATIONS

PCT International Search Report PCT/EP2017/069441 Completed: Nov. 15, 2017; dated Nov. 27, 2017 2 pages.

*Primary Examiner* — Joseph M. Pelham

(57) ABSTRACT

A device for emanating materials in the environment, preferably by heat evaporation, including: a supply for materials; an emitter of materials, for emitting the materials from the supply to surrounding environment, by application of power from a power supply according to an operation mode; an operation mode adjusting mechanism for adjusting the operation mode of the emitter, by controlling the power delivered to the emitter according to a determined transfer function. The transfer function is modular, so that it can be changed or completely replaced while keeping at least partially the adjusting mechanism in the device.

13 Claims, 1 Drawing Sheet

(51) Int. Cl.
*H05B 3/40* (2006.01)
*H05B 3/06* (2006.01)
*H05B 3/02* (2006.01)
*A61L 9/03* (2006.01)
*A01N 25/18* (2006.01)
*H05B 1/02* (2006.01)

(56) References Cited

U.S. PATENT DOCUMENTS

| | | | |
|---|---|---|---|
| 6,169,852 B1* | 1/2001 | Liao | F22B 1/284 |
| | | | 261/142 |
| 6,792,199 B2 | 9/2004 | Levine et al. | |
| 7,281,811 B2* | 10/2007 | Thuot Rann | A61L 9/037 |
| | | | 219/220 |
| 7,352,960 B2 | 4/2008 | Hafer et al. | |
| 2002/0181946 A1* | 12/2002 | Brown | A01M 1/2077 |
| | | | 392/390 |
| 2004/0033171 A1 | 2/2004 | Kvietok et al. | |
| 2004/0035409 A1* | 2/2004 | Harwig | A61L 9/037 |
| | | | 126/96 |
| 2004/0071456 A1* | 4/2004 | Levine | A61L 9/037 |
| | | | 392/395 |
| 2005/0191481 A1 | 9/2005 | He et al. | |
| 2006/0022064 A1 | 2/2006 | Triplett et al. | |
| 2006/0221594 A1* | 10/2006 | Thuot Rann | A61L 9/037 |
| | | | 362/96 |
| 2010/0059601 A1* | 3/2010 | Bankers | A01M 1/2077 |
| | | | 239/44 |
| 2013/0081541 A1 | 4/2013 | Hasenoehrl et al. | |
| 2014/0037273 A1 | 2/2014 | Jaworski et al. | |
| 2014/0093224 A1* | 4/2014 | Deflorian | A01M 1/2077 |
| | | | 392/395 |
| 2016/0150828 A1* | 6/2016 | Goldstein | H05B 6/108 |
| | | | 392/387 |

FOREIGN PATENT DOCUMENTS

| | | | | |
|---|---|---|---|---|
| EP | 0716807 A1 | 6/1996 | | |
| GB | 2404098 A | * | 1/2005 | A01M 1/2077 |
| WO | 200230220 A1 | 4/2002 | | |

\* cited by examiner

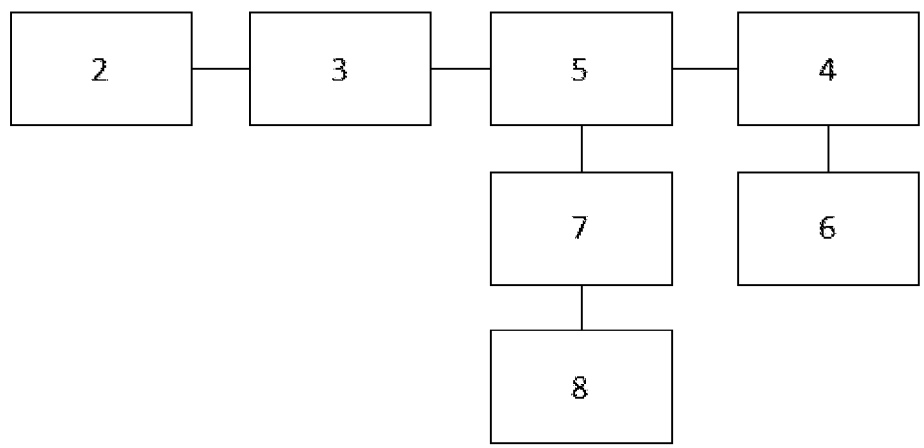

DEVICE FOR EMANATING MATERIALS

FIELD OF THE INVENTION

The present invention concerns a device for emanating materials in the environment.

BACKGROUND OF THE INVENTION

Devices for emanating materials are known, for example out of EP362397A1, which discloses a device with a bottle for containing Material in liquid form, a heater and a wick for transporting the materials from the bottle to the wick. This device is attached to a power socket, and the heater works at a pre-defined power to emanate the materials into environment.

Such devices can emit many different kinds of materials, for instance insect repellents or perfumes.

These prior art devices commonly use PTC as heating elements. An example of a typical heater used in such devices is described in EP0290159 A2, is a resistive heating element with a positive temperature coefficient (PTC). The PTC increases its resistance with increasing temperature, thus self-regulating when connected to a power source. Typically, the PTCs are connected to the mains directly or via purely resistive elements such as a constant resistor, a fuse. A switch may be provided.

So far it the devices for emanating materials have only one constant emission mode. However, different emission modes may be required for different applications.

BRIEF SUMMARY OF THE INVENTION

The present invention aims to solve this problem by using a device for emanating materials in the environment, and a circuit board, for the device, comprising an electronic circuit. The dependent claims concern further advancements of the invention.

The invention concerns a device for emanating materials in the environment, preferably by heat evaporation. The device comprises at least a supply for materials and an emitter of materials, for emitting the materials from the supply to surrounding environment, by application of power from a power supply. The device further comprises an operation mode adjusting means for adjusting operation mode of the emitter, by controlling the power delivered to the emitter according to a determined transfer function. The transfer function is modular, so that it can be changed or completely replaced while keeping at least partially the adjusting means in the device.

A device according to the invention is suitable for emanating a material into the environment. The materials are preferably in liquid form contained in a suitable reservoir, e.g. a plastic or a glass bottle.

The transfer function is configured to gradually and preferably linearly adjust the emission rate of the wick or the temperature of the heater in response to an input voltage. The transfer function can be linear, but preferably contains nonlinear mappings such as exponentials or logarithmic functions for linearizing the heaters response. The transfer function compensates the typically nonlinear thermal response of the heater to a linear change of input current or voltage. For example, the transfer function takes, as input, a desired target temperature T and gives, as output, a power P which must be provided to the heater, for example as pulse width modulated (PWM) voltage signal, in order to yield the desired temperature T. If the response of the heater would be linear, the transfer function could be linear as well, however, since the heater comprises a PTC the temperature does not scale linear but goes into saturation over a rising input voltage which shall be compensated via the transfer function. The transfer function can also be configured to adjust the emission rate instead of the temperature.

The definition for this transfer function can optionally be created and flashed on the device during a manufacturing process or it can be remotely updatable at any time, for example via OTA (over-the-air programming).

Preferably, the device further comprises a transport means for transporting the materials from the reservoir to an emitter. Exemplary transport means transport the material via capillary action, for example the transport means is a wick.

The device preferably contains a housing for supporting its components. The housing preferably suitable for engageably receiving the material reservoir.

The device has an operation mode adjusting means for adjusting the operation mode of the emitter, by controlling the power delivered to the emitter according to a determined transfer function.

The modularity means that the transfer function can be replaced or selected. For instance, a new software routine, which comprises the transfer function but is not the complete software, can be uploaded. The software routine is stored in a memory circuit and executed by a processor, in one preferred instance both the memory circuit and the processor are integrated in a single integrated circuit such as a MCU with memory. The functions can also be pre-stored as circuit or as software, preferably as software. In this case each function is a module and it can be selected between the modules functions. In another instance, the function is a circuit, which can be placed on a socket thus connecting it to the remaining device's circuit. Other way of obtaining the modularity can be envisaged, as long as the transfer function can be changed or completely replaced while keeping at least partially the adjusting means in the device.

In one instance the modularity comes from the set of different configurations of the circuit which can be selected, e.g. via dip-switch, or jumpers.

In one embodiment of the invention, the operation adjusting means is a circuit. Part of the circuit is modular.

In another embodiment of the invention, the operation adjusting means comprises, at least in part, a process defined in the software of a micro controlling unit (MCU). The term software has identical meaning to firmware within the context of the present invention. The software is stored in a memory circuit and executed by a processor, in one preferred instance both the memory circuit and the processor are integrated in a single integrated circuit such as a MCU with memory.

In the most simple configuration of the invention, the circuit has a constant operation mode, meaning a constant emission profile, meaning that the power at the emitter, is constant, and given constant room conditions, and sufficient volume in the environment, the material will be emanated at a constant rate. In this mode, the operation mode adjusting means is constant. Fabrication of this first device is simple, because everything is fixed to a single operation mode.

In another exemplary operation mode, the emitter power is set to a first power at times where certain mosquitos flight most, such as dawn and dusk, and at a second power on the remaining day, the second power being lower than the first power.

However, if a device is required to work under different conditions, e.g. at a lower temperature in another geographical region, which is known for having mosquitos more sensitive to a certain repellent, then a modification of the device will need to be implemented. The same first device cannot be used, because it is meant only to the first condition. If the device is made according to the invention, then the device only need to have its modular transfer function replaced. For instance, only part of a memory accessible by the MCU can be changed, this could be as low as a single Byte, telling the MCU to use another pre-programmed transfer function, or it can be the transfer function itself, for example between 40 bytes and 20 kBytes. Preferably, the transfer function occupies less than 10% of the storage capacity needed for the complete software size. Due to the modularity of the transfer function, the change can be made without requiring to change the circuit, e.g. installing another PCB, or reprogramming completely the MCU. The modularity enables a low quantity of memory necessary to be changed, therefore the changes can be made very quickly, even during production, without considerably affecting the production cycle, if at all.

In an advantageous mode of the invention, only a restricted set of data can be received as part of the transfer function. This data consists only of non-executable code, for instance only the selection data. An especial advantage of this embodiment of the invention, is that only this data (e.g. the selection data) is transmitted while the transfer function(s) is (are) pre-programmed, thus avoiding mishandling or non-foreseen uses of the device, since the transfer function itself cannot be tampered with via the setting means.

In an exemplary device, wherein the operation mode is a constant emission, the power (P) is a function of the transfer function (P=f(T), wherein T is the temperature). By selecting T from T1 to T2(T2=0.9×T1), i.e. 90% of the original temperature T1, the transfer function (f(T)) makes sure that the power output (P) is adjusted such that the heating element is set at a temperature T2.

In a preferred embodiment the device has a variable operation mode. Given a certain input, such as from a user or a pre-defined programming, the relative power is changed.

The operation mode adjusting means (a( )) for adjusting operation mode (g( )) of the emitter, by controlling the power delivered to the emitter according to a determined transfer function (f( )) can be exemplary described as:

$P=a(g(\ )f(\ ))$

In a preferred case $P=f(g(x),y)$

Wherein the variable x is preferably one of temperature (T), evaporation rate (R), relative power (rP). f( ) can depend from other variables or constants as well (y), for instance a constant to adjust to the materials ability to be evaporated. In this case the modularity is given by selecting f( ) and/or y.

The transfer function can also be configured to adjust the emission rate instead of the power, the conversion to power being done by another module. The transfer function can be linear, preferably contains exponentials or logarithmic functions for linearizing the heaters response.

In a further development of the invention, the device further comprises means for setting the transfer function, between at least two pre-determined transfer functions. These means allow for selecting a transfer function and/or at least a constant of the transfer function out of a predetermined selection. For instance, a first transfer function is programmed to downrate the output power of the heater by a first factor, e.g. 70%, of the maximum rated power of the heater; a second transfer function is programmed to downrate the output power of the heater by a second factor, e.g. 85%; yet a third transfer function is programmed to downrate the output power of the heater by a third factor, e.g. 100% (allowing for maximum rated power of the heater). In one embodiment the means for setting the transfer function is a switch (e.g. a dip-swith), the pre-selection could be circuit components or even partial circuits, the switch being configured to switch between the components. Examples are the selection of different resistors or capacitors, or RC components, in a circuit, either by selecting exclusively or adding/subtracting components. In a preferred embodiment, the means for setting the transfer function is a programmable memory preferably including a configuration programming function in the MCU, which is able to obtain a setting command, and upon the correct command set the pre-determined function accordingly.

Preferably, the device comprises an electronic communication interface, configured to receive and transfer a setting command to the setting means, the setting command carrying the information of a desired selection of the predetermined selection. Examples of the electronic communication interface are WIFI-interface, I2C-interface, RS232-interface, or Bluetooth-interface. The programmable memory is preferably programmable multiple times, e.g. as an EEPROM, SRAM, FLASH. A wired electronic interface has the advantage that the transfer function can be set on production line, e.g. at the time of the electrical testing the circuit board. A wireless interface has the advantage that the transfer function can be set, e.g. when a user first powers the device, such that the device can be configured to the respective region.

In a variation of the setting means as previously described, it is configured to receive a new transfer function from external, preferably via the electronic communication interface, thus adding or replacing the received transfer function with the existing one. It also can add a transfer function on a first configuration step, when the device still has no transfer function.

With the setting means, the transfer function can be set out of a selection, without needing to upload a complete new software, thus speeding up production and/or reconfiguration of the device.

In one very advantageous embodiment of the invention, the emitter is a PTC. A PTC heater may work automatically, e.g. at 110 V and 220 V from the mains. However, a circuit with a certain operation mode that is configured to control the power at 80% of the PTC nominal power at 110 V, will not work at 220 V, due to the non-linearity of the PTC. This can be easily overcome with the present invention by selecting another transfer function for the 220 V. Thus, a replacement of the device is not needed.

The device according to the invention preferably has a housing, the setting means is preferably comprised in the housing, further preferably comprised in the main circuit board.

BRIEF DESCRIPTION OF THE DRAWINGS

FIG. 1 shows a schematic diagram on one device embodiment according to the invention.

DETAILED DESCRIPTION OF THE INVENTION

While in the description above PTC was used as emitter, it is to be understood that any suitable emitter can be used, preferred emitters are of the heating time, and the main advantages have been obtained with the PTC. With the present invention, it is possible to drive PTC at any other suitable operation point other than the nominal.

Housing

The housing defines the overall shape of the device, with walls defining an interior. The housing may be comprised of any suitable housing material such as metal, plastic, glass or fiberboard, or combinations thereof, with blowmolded or injection-molded plastic being most preferred and practical housing materials of construction. It is important to note that the overall housing may be comprised of housing portions that are separately molded and later assembled to define the overall shape to the device, and which can provide for structural complexity inside and outside of the overall shell of the device. For example, housing portions may be screwed together, or fit together with plastic protrusions and holes, or sonically welded together to form the overall housing.

The shape of the housing may be cylindrical, or more box or block-like in shape, or may be some other practical and appealing overall shape, and may include various interior shelves, recesses and mounting surfaces for various interior components, along with contours, colors and exterior ornamentation for aesthetic reasons. Overall, the housing is essentially a container with walls that define an interior space in which various components of the present device (printed circuit board, etc.) may be placed and held. As mentioned, the configuration of the housing, and the placement of the components therein, may lead to various degrees of user accessibility for each of the particular components. The most preferred materials of construction for the housing of the present invention are polyethylene, polypropylene, polybutylene, polybutylene terephthalate, polystyrene, polycarbonate, polyvinyl chloride, and polyethylene terephthalate, or mixtures thereof, wherein the preferred plastic materials are blow-molded, injection blowmolded, injection molded, and/or thermoformed to create the various shapes of the housing portions. The housing may be created to appear opaque or transparent (in part or in whole) and may be constructed of any color (e.g., white or beige or some decorative color). Construction from injection-molded plastic allows for transparent/clear, transparent/colored, or opaque/colored plastic parts, further allowing wide variation of functionality and aesthetic appeal.

Main Circuit

The invention also concerns a circuit board, also called main circuit board, for a device as described in the present invention; the board is preferably a printed circuit board (PCB). The board comprises, on it, an electronic circuit having functionally connected to it, at least:

A connector for the emitter of materials;
The operation mode adjusting means;
The means for setting the transfer function.

Preferably, the main circuit board comprises a controlling unit (MCU), a memory circuit which can optionally an integrated circuit into the MCU chip, and an electronic communication interface. The electronic interface comprises at least one antenna, preferably directly on the cupper layer of the PCB. The antenna can also be part of an RF module soldered on the PCB. The electronic communication interface is preferably of the wireless type, being configured to transmit in a certain protocol, e.g. Wifi, Bl E, Zigbee, Thread, IEEE 802.11 a/b/g/n, IEEE 802.15.4 MAC/PHY, IEEE Standard 802.15.4-2003, any Bluetooth 2.4 Ghz ISM band. A part of the electronic communication interface can be integrated in the same circuit as the MCU.

In one preferred mode of the invention, the heater is powered by the mains, after a half or full wave rectifier, and is further preferably driven by a MOSFET, preferably in switching mode.

Panel

The device preferably comprises a panel, which further comprises a sign able to transmit information to a user. The panel further preferably comprises at least one button.

Light Source for the Indicia Means

For example, the light source may be one or more LED's (light emitting diodes). Non-limiting examples of preferred LED's include bicolor LED's, or dual 2-color LED assemblies, SMD LED's, micro LED's, 3-10 mm LED's, rectangular LED's, single color LED's, infrared LED's, right-angle LED's, blinking LED's, and the like. A preferred example is an RGB LED. The preferred LED may be chosen on the basis of: the particular events or status that requires signaling to the user, (for example, "ON", and/or "end-of-life" of the material). The electronics, (including printed circuit board (PCB) design, cost, compatibility of the LED with other electronic components, current/voltage requirements etc); and, the physical layout of the PCB, its size constraints, location and orientation within the housing of the device, (for example, orientation of the PCB may dictate the choice between a right-angle LED and a standard LED). Most preferred is to incorporate a suitable LED (such as a bicolor LED or an assembly of LED's) as the light source that may provide one color when the device is vaporizing volatile material (e.g., green, to signal that the device is running rather than off) and a second color to signal when the device is depleted of material (e.g., a red color, or a blinking color).

Environment

Environment corresponds to any defined space, whether open or enclosed by one or more surfaces, walls, ceilings, floors, or other solid or fictitious boundaries, which receives the evaporated material. For example, environment may correspond to a residential room (bedroom, bathroom, kitchen, etc.), commercial space (factory floor, office cubicles, etc.), automotive enclosure (car, truck, recreational vehicle), airline compartment, or any other space in which it is desirable to deliver a vapor.

For all necessary measurements it is considered that the measurements are done under constant room conditions (T=22° C., ambient pressure=1 atm, Relative humidity=50%). For heating, it is considered that the room is sufficiently large so that the heating of a PTC, small relative to the room, does not substantially influence the room's temperature. A sufficient volume in the environment, i.e. sufficiently large room, is considered as 28 cubic meters.

Material

The material is able to be delivered to the surrounding environment, so that its final form in the air is preferably: vapor, mist, gas, particulate suspension, or a mixture of any of these. Preferably, the material can be evaporated. The material has a composition. In one preferable embodiment of the invention, the material has an insecticide composition. In another preferred embodiment of the invention, the material has an air care composition. The term material for the purpose of this invention, refers to the material able to be dispensed, it will become clear when it is to be distinguished from the material of other components of the invention.

In the present invention, evaporated material means the material delivered into the surrounding environment, so that its form in the environment is preferably: vapor, mist, gas, particulate suspension, or a mixture of any of these.

The material in the reservoir for being delivered into the environment may be present from about 1 gram to about 50 grams. Depending on whether the composition is a fragrance or an insecticide or other air treatment mixture, the composition may contain anywhere from trace actives to 100% actives and may contain any number and amount of solvents and/or carriers, volatile or otherwise. For example, the device of the present invention may comprise a volatile material further consisting of only a single volatile chemical such as citronella. In another embodiment of the invention the volatile material may comprise only eucalyptus oil. The material may comprise anywhere from one or a few to up to many active materials dissolved or compounded with solvents and carriers that may or may not be volatile. Most preferred is to utilize volatile mixtures (comprising mixtures of actives and solvents together) wherein all of the components are volatile such that the reservoir will eventually empty of all visible contents after a predetermined use-up period referred to as the "end-of-life". Most preferred is to place from about 5 mL to about 45 mL of a liquid or gelled volatizable material within reservoir.

Material for Insecticide

An insecticide composition according to the present invention may be a pesticide, an insecticide repellent, an insecticide killer, or combinations thereof. Insecticide compositions for use in the present invention are those of the type described in U.S. Pat. No. 4,663,315 to Hasegawa, et al., incorporated herein by reference. Hasegawa describes many useful volatile insecticidal compositions that will work well within the reservoir of the present invention. The preferred active ingredients of the compostion are pyrethroid compounds. Non limiting examples of suitable actives are: Allethrin, Bifenthrin, Cyfluthrin (dichlorovinyl derivative of pyrethrin), Cypermethrin (including the resolved isomer alpha-cypermethrin, dichlorovinyl derivative of pyrethrin), Cyphenothrin, Deltamethrin (dibromovinyl derivative of pyrethrin), Esfenvalerate, Etofenprox, Fenpropathrin, dichlorovinyl derivative of pyrethrin, Prallethrin, Resmethrin, Silafluofen, Sumithrin, tau-Fiuvalinate, Tefluthrin, Tetramethrin, Tralomethrin, Transfluthrin, Fenvalerate, Flucythrinate, Flumethrin, lmiprothrin, lambdaCyhalothrin, Metofluthrin, Permethrin. The composition may comprise one or more different active compounds.

Material for Air Care

For use as a fragrance-dispersing device, fragrance components of the volatazable material for the present invention may comprise one of more volatile organic compounds available from any of the now known, or hereafter established, perfumery suppliers, such as international Flavors and Fragrances (IFF) of New Jersey, Givaudan of New Jersey, Firmenich of New Jersey, etc. Many types of fragrances can be used in the present invention. Preferably the fragrance materials are volatile essential oils. The fragrances, however, may be synthetically derived substances (aldehydes, ketones, esters, etc.), naturally derived oils, or mixtures thereof. Naturally derived fragrance substances include, but are not limited to, musk, civet, ambergis, castoreum and like animal perfumes; abies oil, ajowan oil, almond oil, ambrette seed absolute, angelic root oil, anise oil, basil oil, bay oil, benzoin resinoid, bergamot oil, birch oil, bois de rose oil, broom abs., cajeput oil, cananga oil, capsicum oil, caraway oil, cardamon oil, carrot seed oil, cassia oil, cedar leaf, cedarwood oil, celery seed oil, cinnamon bark oil, citronella oil, clary sage oil, clove oil, cognac oil, coriander oil, cubeb oil, cumin oil, camphor oil, dill oil, estragon oil, eucalyptus oil, fennel sweet oil, galbanum res., garlic oil, geranium oil, ginger oil, grapefruit oil, hop oil, hyacinth abs., jasmin abs., juniper berry oil, labdanum res., lavander oil, laurel leaf oil, lavender oil, lemon oil, lemongrass oil, lime oil, lovage oil, mace oil, mandarin oil, mimosa abs., myrrh abs., mustard oil, narcissus abs., neroli bigarade oil, nutmeg oil, oakmoss abs., olibanum res., onion oil, opoponax res., orange oil, orange flower oil, origanum, orris concrete, pepper oil, peppermint oil, peru balsam, petitgrain oil, pine needle oil, rose abs., rose oil, rosemary oil, sandalwood oil, sage oil, spearmint oil, styrax oil, thyme oil, tolu balsam, tonka beans abs., tuberose abs., turpentine oil, vanilla beans abs., vetiver oil, violet leaf abs., ylang ylang oil and like vegetable oils, etc. Synthetic fragrance materials include but are not limited to pinene, limonene and like hydrocarbons; 3,3,5-trimethylcyclohexanol, linalool, geraniol, nerol, citronellol, menthol, borneol, bomeyl methoxy cyclohexanol, benzyl alcohol, anise alcohol, cinnamyl alcohol, (3-phenyl ethyl alcohol, cis-3-hexenol, terpineol and like alcohols; anethole, musk xylol, isoeugenol, methyl eugenol and like phenols; a-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, citral, citronellal, hydroxycitronellal, benzaldehyde, methyl nonyl acetaldehyde, cinnamic aldehyde, dodecanol, a-hyxylcinnamic aldehyde, undecenal, heliotropin, vanillin, ethyl vanillin and like aldehydes; methyl amyl ketone, methyl (3-naphthyl ketone, methyl nonyl ketone, musk ketone, diacetyl, acetyl propionyl, acetyl butyryl, carvone, menthone, camphor, acetophenone, p-methyl acetophenone, ionone, methyl ionone and like ketones; amyl butyrolactone, diphenyl oxide, methyl phenyl glycidate, gamma.-nonyl lactone, coumarin, cineole, ethyl methyl phenyl glicydate and like lactones or oxides; methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myri state, methyl myri state, ethyl benzoate, benzyl benzoate, methylcarbinylphenyl acetate, isobutyl phenylacetate, methyl cinnamate, cinnamyl cinnamate, methyl salicylate, ethyl anisate, methyl anthranilate, ethyl pyruvate, ethyl a-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobomyl acetate, linalyl acetate, methyl anthranilate, methyl dihydrojasmonate, nopyl acetate, (3-phenylethyl acetate, trichloromethylphenyl carbonyl acetate, terpinyl acetate, vetiveryl acetate and like esters, and the like. Suitable fragrance mixtures may produce a number of overall fragrance type perceptions including but not limited to, fruity, musk, floral, herbaceous (including mint), and woody, or perceptions that are in-between (fruity-floral for example). Typically, these fragrance mixtures are compounded by mixing a variety of these active fragrance materials along with various solvents to adjust cost, evaporation rates, hedonics and intensity of perception. Well known in the fragrance industry is to dilute essential fragrance oil blends (natural and/or synthetic) with solvents such as ethanol, isopropanol, hydrocarbons, acetone, glycols, glycol ethers, water, and combinations thereof, and using solvent up to as much as 90% of the volatile fragrance composition. Thus, a preferred fragrance composition for use as the volatizable composition in the present invention is comprised of a mixture of many fragrance actives and volatile solvents, sometimes along with smaller amounts of emulsifiers, stabilizers, wetting agents and preservatives. More often than not, the compositions of the fragrance mixtures purchasable from the various fragrance supply houses remain proprietary.

Emitter

The material is emitted into the environment by an emitter. Emitter as meant in the present invention refers to a means for emitting of a material in the surrounding environment, so that its final form in the air is preferably: vapor, mist, gas, particulate suspension, or a mixture of any of these. The emitter preferably comprises a means for conversion into the final form, from a fluid, preferably liquid, source. It is preferred that the emitter is a heater, such as a resistive heater, which can heat the material such that it evaporates. Most preferred is a PTC configured to have its heating dissipation at a temperature that is still within an acceptable limit for the device, for example to avoid combustion of the material, or melting of any plastic component.

Resistive Heater

Resistive heaters are well known in the art and may comprise a single resistor, a plurality of resistors run in series or parallel, thin film heating "traces", induction coils, or any other means for electrically generating heat from electrical current. Such heating elements are amply discussed in both U.S. Pat. No. 6,792,199 to Levine, et al, and European Patent Application EP716807 to Zobele, both incorporated herein in their entireties. Preferred heaters also include "thin-film" resistive heaters, although most preferred for use in the present invention is a standard resistive heater, either a single resistor, e.g. ceramic or standard resistor encased in a hollow ceramic block, or a plurality of resistors connected in series as described in U.S. Pat. No. 7,352,960 to Hafer et al., also incorporated herein in its entirety.

Emission Rate

The average emission rate Er_m over a period of use of at least 1 h, is preferably given by 3 nL/s≤Er_m≤20 nL/s.

Reservoir

In the present invention, the reservoir, preferably a refill bottle, comprises a plastic material that is compatible with the material to be emitted into the environment. It is understood that the reservoir comprises the material, unless specifically stated, such as empty reservoir. A cartridge or other equivalent container is also to be understood as refill bottle according to the invention. For example, refill bottle may be formed of polypropylene, barex and/or PET. However, in certain applications, it may be desirable for the bottle to be formed of other materials such as glass or the like. Preferably, the bottle is suitably sized for use in connection with household use. In accordance with various aspects of the invention, bottle is preferably configured for receipt of between 25 to about 75 milliliters of liquid material. The weight and moment of the device of the present invention, inclusive of the reservoir bottle is preferably such that the center of gravity is appropriately positioned, and the weight is less than that which would otherwise cause the device to be unstable in the electrical outlet.

Supply Means

The device for emanating product has a supply means for supplying material to the emitter. The supply means preferably comprises a mechanical attachment means (fitment) to which a reservoir, such as a refill bottle, can be attached. An example for the fitment is suitable molded plastic collar that snaps over the opening of the refill bottle to adapt the reservoir opening to a smaller hole that accepts and seals around the wick. The fitment also provides a better sealing platform for a screw cap. Such a screw cap can then be used to seal the bottle and wick together (a so-called "witch hat" shaped cap that covers the exposed end of the wick and seals down around the neck fitment and the screw threads of the bottle). Such configurations for the reservoir, fitment, porous wick and screw cap assembly are well described in U.S. Patent Application Publications 2006/0022064 to Triplett, et al. and 2005/0191481 to He, et al., along with PCT Application Publication WO/2002030220 to He, et al, all incorporated herein in their entireties. In order to effect emanating of the material from the emitter of the present device, the wick is positioned in close proximity to the previously described emitter, such as a resistive heating element. In this way, when the resistive element is energized, the emitted heat will warm the saturated porous wick, vaporizing the material. To achieve the alignment of the reservoir such that its wick is placed into close proximity to the heating element, a guidance device as that claimed in U.S. Pat. No. 6,104,867 to Stathakis, et al. may be readily employed within the design of the housing of the present invention.

Transport Means

Preferably, the device comprises a transport means for allowing the transport of material from the supply means to the emitter. The transport means may extend into reservoir. In a preferred embodiment, the transport means is a wick that extends to the bottom of the reservoir, when in operational position, to ensure complete emptying. Suitable wick materials include cellulose fiber bundles, porous sintered plastic, wood, ceramics, graphite, and synthetic fiber bundles, and combinations of these materials, but as mentioned, the porous sintered plastic wicks are highly preferred.

Figures

FIG. 1 shows a schematic diagram on one device embodiment according to the invention. The device comprises an emitter (2), a power circuit (3), and an operation mode adjustment means (4) which controls the operation mode of the power circuit (3) via a transfer function (5). Other relations between the operation mode adjustment means (4) and the transfer function (5) are also envisaged in the present invention, as long as there is a functional relation between both. The device further comprises a means for setting the transfer function (7). Preferably the device further comprises an electronic communication interface (8), configured to receive and transfer a setting command to the setting means. There can also be a communication interface (6) interacting with the adjustment means (4).

In another example according to the invention, the device (1) for emanating materials in the environment, is a liquid evaporator for insecticide. The supply for materials is a reservoir in bottle shape comprising a material that evaporates when heated, a wick is connected to the reservoir. The emitter, for emitting the materials from the supply to surrounding environment, is preferably a PTC heater. It heats the end of the wick, which is not in the bottle by application of power from a power supply. The operation mode adjusting means (a( )) is configured to adjust an operation mode of the emitter, by controlling the power delivered to the emitter according to a determined transfer function (f( )) and according to the operation mode (g( )). The operation modes the present example are Off, Normal, and Boost modes. The heater's power is controlled by pulse-width-modulation (PWM), on a pre-determined transfer function. The transfer function makes sure that a linear change to its input corresponds to a linear change in dissipated power of the PTC, within the PTC's nominal limits. This is necessary due to the high non-linearity of such kind of highly self-limiting heaters. The modular part of the transfer function is this case is a constant, which is set during production. For devices to be operated at 220V mains, the transfer function is set to 1 (8 bits unsigned char 255), via a IEEE 802.11 electronic communication interface (8), right after the quality control step. For devices to be operated at 110V mains, the transfer function is set to 0.85 (8 bits unsigned char 216). Yet, for devices to be operated at 127V, the transfer function is set to 0.8 (8 bits unsigned char 204). In this example, the electronic communication interface (8) receives the command to reprogram a single memory position, in this case a single byte.

In another variation of the example above, the device (1) has programmed a pre-selection of 3 transfer functions in respective memory positions in a memory circuit, each transfer function (5, f( )) is for a different heating element. The electronic communication interface is configured to receive and transfer a setting command. The transfer function to be used is then selected according to this setting command. Therefore, the same main circuit board can be used, for different devices, only a smaller setting command is needed to adapt the board and/or device to its heater. For instance, the board can be used to control a device, which is an insecticide to evaporate a first formulation, a send emanatory that requires a different PTC and a different temperature, and a second scent emanatory with a different temperature from the previous one.

What is claimed is:

1. A device for emanating materials in the environment comprising:
   a supply for materials;
   an emitter of materials, for emitting the materials from the supply to surrounding environment, by application of power from a power supply according to an operation mode;
   an operation mode adjusting means for adjusting the operation mode of the emitter, by controlling the power delivered to the emitter according to a determined transfer function;
   wherein the transfer function is modular, so that it can be changed or completely replaced while keeping at least partially the adjusting means in the device; and
   wherein the transfer function is nonlinear to compensate for a nonlinear response of the emitter to the application of the power.

2. The device according to claim 1, further comprising means for setting the transfer function between at least two pre-determined transfer functions.

3. The device according to claim 2, wherein the device comprises a housing, and the at least two pre-determined transfer functions are comprised within the housing.

4. The device according to claim 3, wherein the setting means is a switch and the at least two pre-determined transfer functions are circuit components, the switch being configured to switch from between the circuit components.

5. The device according to claim 3, wherein the setting means is a software routine and the is at least two pre-determined transfer functions are stored in respective memory positions in a memory circuit.

6. The device according to claim 2, further comprising an electronic communication interface configured to receive and transfer a setting command to the setting means, the setting command carrying the information of a desired selection of the predetermined selection.

7. The device according to claim 6, wherein the electronic communication interface is configured to receive at least part, or the whole transfer function, and wherein the setting means is able to store the function at a determined memory location.

8. A circuit board for a device according to claim 1, the board comprising an electronic circuit having functionally connected to it at least:
   a connector for the emitter of materials;
   the operation mode adjusting means;
   the means for setting the transfer function.

9. The device according to claim 1, wherein the emitter emanates materials in the environment by heat evaporation.

10. The device according to claim 2, further comprising means for setting the transfer function by selecting the transfer function and/or at least a constant of the transfer function out of a predetermined selection.

11. The device according to claim 6, wherein the setting command is limited to a restricted set of data comprising only a selection between the at least two pre-determined transfer functions.

12. The device according to claim 2, wherein the at least two pre-determined transfer functions include a first transfer function configured for use if the power supply is 110 V and a second transfer function configured for use if the power supply is 220 V.

13. The device according to claim 1, wherein the transfer function is configured to gradually or linearly adjust an emission rate of the emitter or a temperature of a heating element thereof.

* * * * *